United States Patent [19]

Chu et al.

[11] Patent Number: 5,077,279
[45] Date of Patent: Dec. 31, 1991

[54] 3'-AZIDO-2',3'-DIDEOXY-5-METHYLCYTI-DINE ANTI-VIRAL COMPOSITION

[75] Inventors: Chung K. Chu, Athens; Raymond F. Schinazi, Decatur, both of Ga.

[73] Assignees: University of Georgia Research Foundation, Inc., Athens; Emory University, Atlanta, both of Ga.

[21] Appl. No.: 534,523

[22] Filed: Jun. 6, 1990

Related U.S. Application Data

[63] Continuation-in-part of Ser. No. 362,756, is a continuation-in-part of Ser. No. 159,246, Feb. 23, 1988, abandoned, which is a continuation-in-part of Ser. No. 16,136, Feb. 18, 1987, Pat. No. 4,841,039, which is a continuation of Ser. No. 857,947, May 1, 1986, Pat. No. 4,681,933, and Ser. No. 104,438, Oct. 2, 1987, Pat. No. 4,916,122, Continuation-in-part of Ser. No. 7,473, Jan. 28, 1987, abandoned.

[51] Int. Cl.$^5$ .............................................. A61K 31/70
[52] U.S. Cl. ............................................ 514/49; 514/51
[58] Field of Search .......................... 514/46, 49, 50, 51

[56] References Cited

U.S. PATENT DOCUMENTS

| | | | |
|---|---|---|---|
| 3,775,397 | 11/1973 | Etzold et al. | 514/49 |
| 3,817,982 | 6/1974 | Verheyden et al. | 536/23 |
| 4,071,680 | 1/1978 | Cook | 536/23 |
| 4,093,715 | 6/1978 | Lin et al. | 514/49 |
| 4,093,716 | 6/1978 | Lin et al. | 514/49 |
| 4,128,639 | 12/1978 | Lin et al. | 514/49 |
| 4,210,638 | 7/1980 | Greer | 514/49 |
| 4,230,698 | 10/1980 | Bobek et al. | 514/49 |
| 4,331,662 | 5/1982 | Eckstein et al. | 514/49 |
| 4,522,811 | 6/1985 | Eppstein et al. | 514/2 |
| 4,604,382 | 8/1986 | Lin et al. | 514/49 |
| 4,710,492 | 12/1987 | Lin et al. | 514/49 |
| 4,724,232 | 7/1988 | Rideout et al. | 514/50 |
| 4,780,453 | 10/1988 | Rideout et al. | 514/50 |
| 4,788,181 | 11/1988 | Driscoll et al. | 514/49 |

FOREIGN PATENT DOCUMENTS

| | | |
|---|---|---|
| 8630189 | 10/1986 | European Pat. Off. |
| 8810354 | 10/1988 | European Pat. Off. |
| 88303248.4 | 10/1988 | European Pat. Off. |
| 224490A1 | 7/1985 | Fed. Rep. of Germany |
| 3608606A1 | 8/1986 | Fed. Rep. of Germany |

OTHER PUBLICATIONS

Sandstrom et al., Drugs 34:372–390, 1987.
Mitsuya et al., J. Sci. Soc., pp. 277–288, 1985.
Herdewijn et al., J. Med. Chem. 30, 1270 (1987).
Herdewijn et al., J. Med. Chem. 31, 2040 (1988).
Lin et al., J. Med. Chem. 30, 440 (1987).
Lin et al., J. Med. Chem. 26, 1691 (1983).
Alcina et al., Antimicrob. Agents and Chemother. 32(9), 1412 (1988).
Alarcon, et al., Antimicrob. Agents and Chemother. 32(8), 1257 (1988).

(List continued on next page.)

Primary Examiner—John W. Rollins
Attorney, Agent, or Firm—Kilpatrick & Cody

[57] ABSTRACT

A composition delivering an HIV-inhibitory amount of an active compound of the general formula:

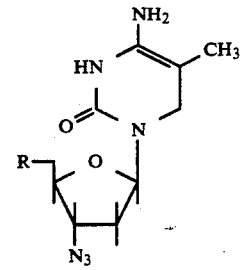

wherein R is OH, monophosphate, diphosphate, or triphosphate, or a pharmacologically acceptable salt thereof; and wherein the means is a pharmaceutically acceptable carrier. In the preferred embodiment, an effective dose of 3'-azido-2',3'-dideoxy-5-methylcytidine, or its derivatives, is administered in a pharmaceutically acceptable carrier to a patient for the treatment of AIDS.

8 Claims, 5 Drawing Sheets

OTHER PUBLICATIONS

Anzai et al., *Agr. Biol. Chem.* 37(2), 345 (1973).
Balzarini et al., *Mol. Pharmacol.* 32, 162 (1987).
Brubaker et al., *Chem. Abstr.* 102:226110x (1985).
Busson et al., *Nucleic Acids Symp. Ser.* 9, 49–52 (1981) (*Chem. Abstr.* 96:69346s (1982)).
Camarasa et al., *J. Med. Chem.* 28, 40 (1985).
Chu et al., *J. Med. Chem.* 21(1), 96 (1978).
Classon et al., *Acta Chemica Scandinavica* B36, 251 (1982).
Colla et al., *Eur. J. Med. Chem.-Chim. Ther.* 20(4), 295 (1985).
DeClercq, *Meth and Find Exptl Clin Pharmacol* 2(5), 253–267 (1980).
DeClercq, *Curr. Chemother. Immunother., Proc. Int. Congr. Chemother.*, 12th 1981 1062 (1982) (*Chem. Abstr.* 97:174446t (1982)).
Dyatkina et al., *Bioorg. Khim.* 12(2), 408 (1986) (*Chem. Abstr.* 105:227205f (1986)).
Dyatkina et al., *Bioorg. Khim.* 9, 132 (1983).
Fox et al., *Herpes Viruses and Virus Chemotherapy*, Elsevier Science Publishers B.V. (Biomedical Division) 53–56 (1985).
Furman et al., *Proc. Natl. Acad. Sci., U.S.A.* 83, 8333 (1986).
Krentisky et al., *J. Med. Chem.*, 26(6), 891 (1983).
Lin et al., *Biochem. Pharmacol.*, 36, 2713 (1987).
Lin et al., *J. Med. Chem.* 26, 544 (1983).
Lin et al., *J. Med. Chem.* 21(1), 109 (1978).
Lin et al., *Biochem. Pharmacol.*, 36, 311 (1987).
Mitsuya et al., *Proc. Natl. Acad. Sci. U.S.A.*, 82, 7096 (1985).
Mitsuya and Broder, *Proc. Natl. Acad. Sci. U.S.A.* 83, 1911 (1986).
Roseman et al., *J. Am. Chem. Soc.*, 83, 659 (1961).
Schinazi et al., *Antimicrob. Agents and Chemother.* 22(3), 499 (1982).
Schinazi et al., *Antimicrob. Agents and Chemother.* 28(4), 552–560 (1985).
Schinazi et al., *Antimicrob. Agents and Chemother.* 30(3), 491 (1986).
Schinazi et al., *Antimicrob. Agents and Chemother.* 32(12), 1784 (1988).
Schinazi et al., *J. Cellular Biochemistry* P405, 74 (1987).
Schinazi et al., "Anti-Human Immunodeficiency Virus (HIV-1) Activity of 3'-Azido-2',3'-Dideoxyuridine in Different Cell LInes".
Shealy et al., *J. Heterocyclic Chemistry* 13(5), 1015 (1976).
Vrheyden et al., *Chem. Abstr.* 81:63942b (1974).
Zaitseva et al., *Bioorg. Khim.* 10(5), 670 (1984) (*Chem. Abstr.* 101:192378c (1984)).
Broder, Modern Concepts and Therapeutic Challenges, *AIDS*, p. 303, Marcel Dekker, Inc., New York, 1987.
DeClercq, *J. Med. Chem.* 29(9), 1561 (1986).
Fischl et al., *New England Journal of Medicine* 317(4), 192 (1987).
Mitsuya et al., Nature, 325, 773 (1987).
Yarchoan et al., *New England Journal of Medicine* 316, 557 (1987).
Chu et al., *J. Med. Chem.*, vol. 32, No. 3, Mar. 1989, pp. 612–617.
Lin et al., *J. Med. Chem.*, vol. 31, No. 2, Feb. 1988, pp. 336–340.
Galegov et al., *Mol. Biol.*, vol. 22, No. 3, 1988, pp. 802–806.
Dyatkina et al., *Bioorg. Khim.*, vol. 12, No. 8, 1986, pp. 1043–1053.

3'-AZIDO-2',3'-DIDEOXY-5-METHYLCYTIDINE ANTI-VIRAL COMPOSITION

BACKGROUND OF THE INVENTION

The U.S. Government has rights in this invention arising out of a Veterans Administration Merit Review Award.

This is a continuation-in-part of U.S. Ser. No. 07/362,756 entitled 3'-Azido-2',3'-Dideoxy-5-Methyl-Cytidine" filed June 7, 1989 by Chung K. Chu and Raymond F. Schinazi, which is a continuation-in-part of U.S. Ser. No. 07/159,246 entitled "2',3'-Dideoxynucleosides as Anti-Retroviral Compositions and Their Method of Preparation", filed Feb. 23, 1988, now abandoned, which is a continuation-in-part of (1) U.S. patent application Ser. No. 07/016,136 entitled "2',3'-Dideoxy-5-Substituted Uridines and Related Compounds as Antiviral Agents" filed Feb. 18, 1987 by Chung K. Chu and Raymond F. Schinazi, now U.S. Pat. No. 4,841,039, which is a continuation of U.S. Ser. No. 06/857,947 filed May 1, 1986 by Chung K. Chu and Raymond F. Schinazi, now U.S. Pat. No. 4,681,933, and (2) U.S. patent application Ser. No. 07/104,438 filed Oct. 2, 1987 entitled "3'-Azido-2',3'-Dideoxyuridine Antiviral Composition" by Chung K. Chu and Raymond F. Schinazi, now U.S. Pat. No. 4,916,122, which is a continuation in part of U.S. Ser. No. 07/007,473 filed Jan. 28, 1987 entitled "3'-Azido-2',3'-Dideoxypyrimidines and Related Compounds as Antiviral Agents", now abandoned.

The present invention is in the field of pharmaceutical delivery systems, and in particular relates to the use of 3'-azido-2',3'-dideoxy-5-methylcytidine and compositions thereof for the inhibition of human immunodeficiency viral infections.

AIDS was recognized as early as 1979. The number of cases reported to the Centers for Disease Control (CDC) has increased dramatically each year since then, and in 1982 the CDC declared AIDS a new epidemic. AIDS is generally accepted at this time to be a consequence of infection with the retrovirus, human immunodeficiency virus (HIV-1). Antibodies to these viruses are present in over 80% of patients diagnosed as having AIDS or pre-AIDS syndrome, and have been found with high frequency in identified risk groups.

A patient is generally diagnosed as having AIDS when he develops an impaired T-cell immunity, usually appearing over a period of eighteen months to three years. As a result of this impaired immunity, the patient becomes susceptible to opportunistic infections, various types of cancer such as Kaposi's sarcoma, and other disorders associated with reduced functioning of the immune system.

HIV is a retrovirus. The genetic material in retroviruses is single stranded RNA, not DNA as in most organisms, which is converted into double stranded DNA for expression of the encoded genes by two enzymes, a polymerase and ribonuclease, referred to collectively as reverse transcriptase. The DNA is then integrated into the cell's genome, where it can remain indefinitely, or be expressed for viral replication. The virus preferentially infects T4 lymphocytes, a subset of the immune system. However, it also infects cells in the nervous system and intestine and some bone-marrow cells. The virus can remain latent for years, or undergo rapid replication, destroying the host cells.

Most compounds presently in use target the replication of the viral nucleic acids, although efforts are being made to vaccinate individuals against the virus and to interfere with the infection process. A number of compounds have been found to have antiviral activity against this virus, including HPA-23, interferons, ribavirin, phosphonoformate, ansamycin, suramin, imuthiol, penicillamine, rifabutin, AL-721, 3'-azido-3'-deoxythymidine (AZT), and other 2',3'-dideoxynucleosides, such as 2',3'-dideoxycytidine (DDC), 2',3'-dideoxyadenosine (DDA), 3'-azido-2',3'-dideoxyuridine (AzddU), 2',3'-didehydrocytidine, 3'-deoxy-2',3'-didehydrothymidine and 3'-azido-5-ethyl-2',3'-dideoxyuridine (AzddU).

In general, antiviral agents are inhibitors of viral replication, but such agents are usually quite toxic for the host as well. Most of the antiviral drugs that have been discovered so far cannot be prescribed for a prolonged period of time because of their toxicity. It is difficult to screen in vivo for toxicity, especially long term toxicity.

For example, AZT was initially thought not to be toxic when tested in vitro, but was subsequently determined to have bone-marrow toxicity when administered for periods of several months. Richman et al. has shown that because of AZT-associated hematological abnormalities, twenty-one percent of patients undergoing AZT therapy required multiple blood transfusions during the six month treatment period. Bone marrow depression may be due to the accumulation of phosphorylated AZT within cells, which may result in a substantial depression of thymidine 5'-triphosphate pools. Another drawback of AZT is its short half life in humans (about 1.1 hour) and its elimination in urine as 3'-azido-3'-deoxy-5'-glucuronylthymidine, a metabolite with no substantial antiviral activity.

Many compounds have been reported as having antiviral activity in vitro, although there is a difference in opinion even as to the validity of this data, depending on the test system. The Food and Drug Administration requires in vivo toxicity testing and pharmacokinetic studies before they will consider an application for an Investigational New Drug License. Many times a compound is predicted to be useful in the treatment of AIDS, based on this data, only to be discarded as soon as these studies are conducted. For example, Chu, et al., reported in *J. Med. Chem.* 32, 612–617 (February, 1989), that a number of pyrimidine nucleosides related to AZT have activity against HIV, in vitro, and limited toxicity in vitro in human peripheral blood mononuclear cells. They noted that several were particularly promising, including 3'-azido-2',3'-dideoxyuridine (AzddU), 3'-azido-5-ethyl-2',3'-dideoxyuridine, and 3'-azido-2',3'-dideoxycytidine (AzddC) and its 5-methyl analogue (AzddMeC). Unfortunately, subsequent testing demonstrated that all but the last compound was toxic in vitro using an assay measuring colony formation of human granulocytes-macrophages precursor cells. In particular, AzddU, was determined to be substantially more toxic than AZT; for example, AZT caused a 50% reduction in cells at 1 mM AZT, AzddC caused an 80% reduction; both killed 100% of the cells at 10 mM.

It is also difficult, if not impossible, to predict the bioavailability, the half-life, the stability, and the metabolism of compounds based on in vitro data. Many of the compounds which are not toxic and exhibit in vivo antiviral activity are metabolized quickly into inactive compounds, or have such short half-lives as to be useless. As a result, only with in vivo data can one predict the usefulness of a compound in the treatment of AIDS. Moreover, only with information as to bioavailability and metabolism can one truly determine the dosage and time and means of administration of a compound.

Despite the tremendous amount of research on a cure for AIDS, it is still a fatal disease. Patients infected with HIV still have no hope of a cure, nor are there any drugs which have been demonstrated to be safe and efficacious for long term use.

It is therefore an object of the present invention to provide a new antiviral composition that has low toxicity toward uninfected cells.

It is a further object of this invention to provide a composition for inhibiting the replication of HIV-1 and other related retroviruses.

It is yet another object of the present invention to provide a method for the prevention and treatment of infection by HIV-1 and other retroviruses.

SUMMARY OF THE INVENTION

An antiviral composition which delivers an HIV-inhibitory amount of an active compound of the general formula:

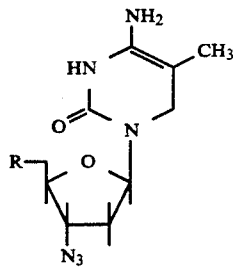

wherein R is OH, monophosphate, diphosphate, or triphosphate, or a pharmacologically acceptable salt thereof; in a pharmaceutically acceptable carrier. Because the composition has been discovered to have two to three times the half-life of AZT, to be converted intracellularly into AZT, and to be preferentially incorporated by peripheral blood mononuclear cells, the composition can be administered less frequently and in higher dosages than AZT, to achieve a greater effect without toxicity. Another advantage of this composition is its highly selective anti-retroviral activity, in combination with low cytotoxicity. The compound is not active against herpes simplex virus type 1 or coxsackievirus B4, and is only weakly active against Friend murine retrovirus. Most importantly, it exhibits no toxicity to erythroid precursor cells when tested up to 100 $\mu$M.

BRIEF DESCRIPTION OF THE DRAWINGS

FIG. 3A, FIG. 3B, and FIG. 3C are graphs of the total clearance (A), renal clearance (B), and non-renal clearance (C) of AzddMeC, as a function of dose (mg/kg), Horizontal lines denote mean values. (◯), 10 mg/kg; (□), 50 mg/kg; and (△), 100 mg/kg intravenous dose.

DETAILED DESCRIPTION OF THE INVENTION

Figure 1:
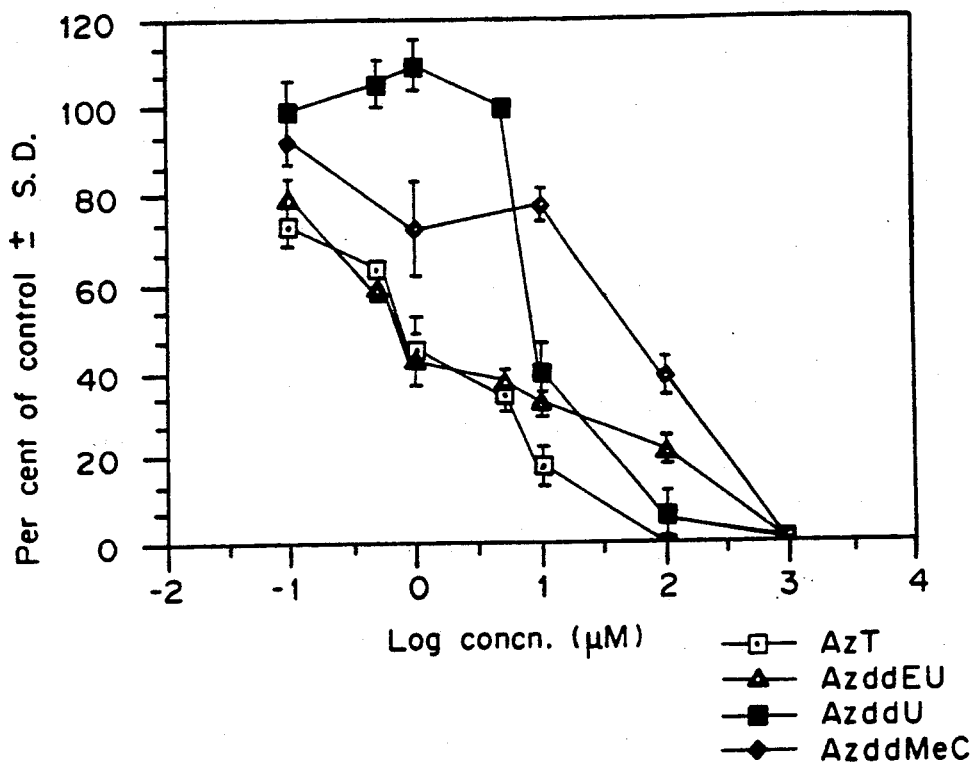
FIG. 1 is a graph showing the relative effect of 3'-azido-3'-deoxythymidine (AZT), 3'-azido-2',3'-dideoxyuridine (AzddU), 3'-azido-5-ethyl-2',3'-dideoxyuridine (AzddEU) and 3'-azido-2',3'-dideoxy-5-methylcytidine (AzddMeC) on colony formation of human granulocytes-macrophage precursor cells.

3'-azido-2',3'-dideoxy-5-methylcytidine, having the general formula:

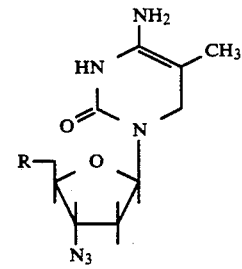

wherein R is OH, monophosphate, diphosphate, or triphosphate, and pharmacologically acceptable salts thereof, in a pharmaceutically acceptable carrier, is administered to patients two to three times a day to achieve a blood concentration of active ingredient of from about 0.2 to 40 $\mu$M. A preferred concentration range is from 0.2 to 20 $\mu$M and most preferably about 1 to 10 $\mu$M. This is equivalent to the administration of from 1 to 60 milligrams of compound per kilogram of body weight per day.

The present invention is based on the discovery that 3'-azido-2',3'-dideoxy-5-methylcytidine (AzddMeC) and phosphorylated derivatives thereof exert a highly selective activity against HIV, while at the same time exhibiting very low toxicity towards normal, uninfected, cells; in combination with an extended half-life; preferential uptake by mononuclear blood cells; and conversion intracellularly into AZT, which is known to be effective in vivo against HIV.

3'-Azido-2',3'-dideoxy-5-methylcytidine is a known compound. See, for example, Lin, et al., *J. Med. Chem.* 26, 1691–1696 (1983). Lin, et al. tested the activity of AzddMeC against L1210 and sarcoma 180 cells in vitro and found that the compound, as well as 3'-azido-2',3'-dideoxycytidine (AzddC), are inactive against both cell lines. Lin, et al., reported that 3'-azido-2',3'-dideoxycytidine exhibits only marginal inhibitory activity toward two particular enzymes isolated from L1210 cells, and that AzddMeC exhibits only modest activity toward the same enzymes. Subsequent reports identified the compound as potentially active against HIV, but did not address the toxicity and half-life in vivo.

AzddMeC can be administered in the form of a pharmaceutically acceptable salt, such as a potassium, sodium, or amine salt. Suitable methods of synthesis of 5-methyl-3'-azido-2',3'-dideoxycytidine are found in the literature and are known to those skilled in the art. See, for example: Lin, et al., *J. Med. Chem.* 26, 1691–1696 (1983); Horowitz, J. P., et al., *J. Org. Chem.* 31, 205 (1966); Horowitz, J. P. et al., *J. Org. Chem.* 32, 817 (1967). Moffatt, J. G., et al. *J. Org. Chem.* 39, 30 (1974); and Robbins, M. et al., *Tet. Letters* 25, 367 (1984).

A specific method of synthesis of AzddMeC according the method of Lin, et al., is provided in Example 1.

EXAMPLE 1

Synthesis of 3'-azido-2',3'-dideoxy-5-methylcytidine (AzddMeC).

5'-O-Acetyl-3'-deoxythymidine (2)

To a pyridine (50 ml) solution of 3'-azido-3'-deoxy-thymidine (5.0 g, 18.7 mmole) 1 was added acetic anhydride dropwise in an ice-water bath. The mixture was allowed to stand overnight in the refrigerator. The solution was then poured into $CHCl_3$ (20 ml), washed with $H_2O$ (200 ml×2), with a saturated solution of sodium bicarbonate and then $H_2O$ (200 ml×2). The organic layer was then dried ($MgSO_4$). After removing the solvent, a syrup (6.5 g) was obtained.

5'-O-Acetyl-3'-azido-2',3'-dideoxy-5-methyl-4-trizolyl-1-(beta-D-ribofuranosyl)pyrimidine (3)

To a pyrimidine (60 ml) solution of compound 2 (6.5 g, 21.04 mmole) was added $Cl-C_6H_4OPOCl_2$ (7.8 g, 31.56 mm) dropwise followed by the addition of triazole (4.35 g, 63.12 mm). The mixture was stirred at room temperature for 7 days. After stirring, methylene chloride (200 ml) was added to the reaction mixture. The resulting solution was washed with $H_2O$ (200 ml×2), saturated sodium bicarbonate solution, and then $H_2O$ again. The organic layer was then dried ($MgSO_4$). Evaporation of solvent gave a yellowish solid (5.04 g).

3'-Azido-2',3'-dideoxy-5-methylcytidine (4, AzddMeC)

Compound 3 (5.04 g, 13.96 mm) was dissolved in 30 ml of ammonium hydroxide-dioxane (1:3). The reaction mixture was stirred at room temperature for 1 hour and then the solvent was evaporated to form a syrup. The resulting syrup was stored in a saturated solution of ammonia in methanol at room temperature overnight. The reaction mixture was then evaporated to dryness and the residue was purified on a silica gel column using $CHCl_3$ and methanol as the eluent, first with a 10:1 ratio and then with a 5:1 ratio. The fractions were combined and evaporated to yield AzddMeC as a solid (4, 2.9 grams).

EXAMPLE 2

Antiviral Activity of AzddMeC

The ability of AzddMeC to inhibit HIV is measured by the inhibition of viral replication in phytohemagglutinin (PHA) stimulated human peripheral blood mononuclear (PBM) cells infected with HIV-1 (strain LAV). Inhibition is determined by measuring the amount of virus-encoded reverse transcriptase. The amount of enzyme produced is compared to an HIV control. The method is described in detail below.

Antiviral Assay in Human Peripheral Blood Mononuclear Cells PBM)

A. Three-day-old phytohemagglutinin-stimulated PBM cells ($10^6$ cells/ml) from hepatitis B and HIV-1 seronegative healthy donors were infected with HIV-1 (strain LAV) at a concentration of about 100 times the 50% tissue culture infectious dose (TICD 50) per ml and cultured in the presence and absence of various concentrations of antiviral compounds.

B. Approximately 45 minutes after infection, 5 ml of the medium, with the compound to be tested, at twice the final concentration in medium, or without compound, was added to the flasks to a final volume of 10 ml. AZT was used as a positive control.

C. The cells were exposed to the virus (about $2 \times 10^5$ dpm/ml, as determined by reverse transcriptase assay) and then placed in a $CO_2$ incubator. HIV-1 (strain LAV) was obtained from the Center for Disease Control, Atlanta, Ga. The methods used for culturing the PBM cells, harvesting the virus and determining the reverse transcriptase activity were those described by McDougal et al. (*J. Immun. Meth.* 76, 171–183, 1985) and Spira et al. (*J. Clin. Meth.* 25,97–99, 1987), except that fungizone was not included in the medium (see Schinazi, et al., *Antimicrob. Agents Chemother.* 32, 1784–1787 (1988)).

The reverse transcriptase activity in the virus-infected control was about $2 \times 10^5$ dpm per ml. Blank and uninfected cell control values were about 300 and 1,000 dpm, respectively. Similar results are obtained when Step C is performed before step B.

D. On day 6, the cells and supernatant were transferred to a 15 ml tube and centrifuged at about 900 g for 10 minutes. Five ml of supernatant were removed and the virus was concentrated by centrifugation at 40,000 rpm for 30 minutes (Beckman 70.1 Ti rotor). The solubilized virus pellet was processed for determination of the levels of reverse transcriptase. Results are expressed in dpm/ml of sampled supernatant.

In vitro macrophage HIV-1 Infection Assay

Monocytes and macrophages were isolated as described by Crowe S., Mills J., and McGrath, M. S., "Quantitative immunocytofluorographic analysis of CD4 surface antigen expression and HIV infection of peripheral blood monocyte/macrophages", *AIDS Res Human Retro.* 3,135–145 (1987), from the buffy coats of blood obtained from the American Red Cross, Atlanta, Ga. The cells were placed in Teflon ™ culture vessels (Savillex, Minnetonka, MN) in RPMI-1640 supplemented with 10% AB-positive (blood group) human serum, at a density of $5 \times 10^5$ cells/ml.

After 7–20 days in culture, while lymphocyte contamination is minimal, macrophages are exposed to HIV-1 (strain HIV-DV) at room temperature for one hour at a multiplicity of infection approximating one $TCID_{50}$ unit/cell. Unbound virus is removed by washing with undiluted fetal calf serum. Cells are then re-suspended and $10^5$ cells/well added to a 96 well microdilution plate in the absence or presence of various drug dilutions in duplicate. Nine days after acute infection, supernatants are harvested and HIV-1 p24 antigen quantitated using the Abbott Laboratories HTLVIII-EIA test. Percent inhibition of p24 in drug treated cells compared with untreated, infected control cells is calculated for all studies.

The median effective ($EC_{50}$) concentrations for various 2',3'-dideoxy- and 2',3'-dideoxydidehydronucleosides, as determined by the median effect method described in *Antimicrob. Agents Chemother.* 30, 491–498 (1986), is based on the percent inhibition of virus, as determined from measurements of reverse transcriptase, plotted versus the micromolar concentration of compound. The $EC_{50}$ is the concentration of compound at which there is a 50% inhibition of viral growth.

AzddMeC has an $EC_{50}$ of 0.081 to 0.22 µM when tested in PBM cells infected with HIV. AzddC is extremely active in human macrophages infected with HIV-1, with an $EC_{50}=0.006$ µM. As used herein, antiviral activity refers to the ability of a composition containing AzddMeC inhibiting the replication of HIV.

AzddMeC was tested against HIV in several cell types and against other viruses for comparison with AZT. The results are shown in Table 1.

TABLE 1

Antiviral activity of AzddMeC and AZT

| Virus | $EC_{50}$ or $IC_{50}$ (µM) AzddMeC | AZT |
|---|---|---|
| HIV-1 (LAV) in PBM cells | 0.09 | 0.002 |
| HIV-1 (DV) in macrophages | 0.006 | 0.0008 |
| HIV-2 (ROD2) in PBM cells | 0.016 | 0.005 |
| HSV-1 (F) in Vero cells | >100 | >100 |
| HSV-2 (G) in Vero cells | >100 | >100 |
| Coxsackievirus (B4) in Vero cells | >100 | >100 |
| Friend retrovirus (EY-10) in SC cells | 2.8 | 0.004 |
| Influenza A (Singapore 1157 (H2N2) and WI 3334-1 (H3N2) in MDCK cells | >100 | ND |

EXAMPLE 3

Cytotoxicity of AzddMeC

The effect of compounds on the growth of uninfected human cells is determined by two assays, one using uninfected peripheral mononuclear cells (PBM) and the other using inhibition of colony formation of granulocytes.

Cytotoxicity in PBM and Vero Cells

Mitogen-stimulated PBM cells ($3.8 \times 10^5$ cells/ml) and vero cells were cultured in the presence and absence of drugs under similar conditions as those used for the antiviral assay described above. The cells were counted after 6 days using a hemacytometer and the trypan blue exclusion method, as described by Schinazi et al., *Antimicrobial Agents and Chemotherapy*, 22(3), 499 (1982). The $IC_{50}$ is the concentration of compound which inhibits 50% of normal cell growth.

AzddMeC is toxic to PBM cells only at a concentration of greater than 200 micromolar.

Toxicity in Vero (African Green Monkey) Cells

Vero cells in growth medium (2.5 ml) were added to 25 cm² flasks (Falcon) in duplicate at a concentration equivalent to one-tenth of cell confluency for each compound under test. After incubation at 37° C. in 5% $CO_2$-95% air for 24 hr, the test compound (2× final concentration dissolved in 2.5 ml of the growth medium), was added. Two flasks were harvested immediately by decanting the medium, washing once with 3 ml of PBS, and then incubating at 37° C. for 5 min with 3 ml of trypsin/EDTA (0.125%/0.02%). The cells dislodged from the flask were generally in clumps and were dispersed by repeated forceful pipetting of the suspension against the surface of the flask. To 1 ml of the well-dispersed cell suspension, 0.2 ml of trypan blue solution was added, and the number of cells were counted using a hemacytometer. This was repeated over the next three days.

This method has previously been described by Schinazi, et al. in "Effect of Combination of Acyclovir and Vidarabine or its 5'-Monophosphate on Herpes Simplex Viruses in Cell Culture and in Mice," *Antimicrob. Agents Chemother.* 22, 499–507 (1982).

AzddMeC is toxic to Vero cells only at a concentration of greater than 400 micromolar.

Cytotoxicity in Granulocytes (bone marrow progenitor cells)

The method used to determine the effect of varying concentrations of compound on human bone marrow progenitor cells is described by Sommadossi, Carlisle, Schinazi and Zhou, in *Antimicrobial Agents and Chemotherapy* 32(7), 997 (1988). Briefly, normal human bone marrow cells are incubated at 37° C. for 2 hours with various concentrations of drug, and cells are washed twice prior to plating. Cell viability is determined by soft-agar cloning and measurement of colony formation.

AzddC exhibits no toxicity to erythroid precursor cells when tested up to 100 µM, making it one of the least toxic nucleoside analogues ever tested in this system.

FIG. 1 is a graph showing the relative effects of 3'-azido-3'-deoxythymidine (AZT), 3'-azido-2',3'-dideoxyuridine (AzddU), 3'-azido-2',3'-dideoxy-5-ethyl-uridine (AzddEU) and 3'-azido-2',3'-dideoxy-5-methyl-cytidine (AzddMeC) on colony formation of human granulocytes-macrophage precursor cells.

The results reported in FIG. 1 clearly show a significant difference in the effect of AzddMeC on colony formation of human granulocytes-macrophage precursor cells in comparison to AZT. At a concentration of 10 micromolar, AzddMeC was less toxic to the cells than AzddU, which is about 20 fold less toxic to these cells than AZT. The in vitro human bone marrow is a good prognosticator of potential problems that may occur in humans administered these nucleosides. (See Sommadossi, Carlisle, *Antimicrob. Agents Chemother.* 31, 452–454 (1987).)

These data demonstrate that AzddMeC has a therapeutic index of greater than 1,000. The therapeutic index of a compound, calculated as $IC_{50}/EC_{50}$, is a measure of the margin of toxicological safety in administering an effective dose of the compound. The low toxicity of this compound could not have been predicted on the basis of chemical structure or prior knowledge in the area of antiviral research.

The cytotoxicity of AzddMeC and AZT were compared:

| $EC_{50}$ or $IC_{50}$ of | (µM AzddMeC) | (µM AZT) |
|---|---|---|
| Cell Type used in Assay: | | - |
| human PBM | >200 | 100 |
| Vero | >400 | 29 |
| MDCK | >100 | ND |
| Human bone marrow: | | |
| GM-CFU | 36 | 0.9 |
| BFU-E | ≧100 | 1.6 |

The discovery that AzddMeC is active against HIV at low concentrations and at the same time quite low in toxicity to normal, uninfected, host cells at the lower concentration is surprising, since AZT, a compound of close structural similarity, exhibits a greater toxicity as measured by various experiments. Moreover, 3'-azido- 2',3'-dideoxy-5-methylcytidine does not substantially inhibit the replication of human bone marrow progenitor cells.

EXAMPLE 4

Inhibition of HIV reverse transcriptase and DNA polymerase α

A recombinant 66,000 D HIV-1 reverse transcriptase was obtained from Dr. S. Hughes at the National Cancer Institute, Frederick Cancer Research Facility, Frederick, MD. This enzyme is reported to have an inhibition profile indistinguishable from the virion-derived enzyme when the effect of different antiviral agents are compared.

The standard reaction mixture (100 μl) for HIV-1 assays contains 100 mM Tris-HCl (pH 8.0), 50 mM KCl, 2 mM MgCl$_2$, 5 mM dithiothreitol, 400 μg/ml BSA, 0.05 U of (rl)$_n$.(dC)$_{12-18}$ per ml (equivalent to 3.1 μg/ml), and 1 μM[$^3$H]dCTP (specific activity 25 Ci/mmol). DNA polymerase α was isolated from PHA-stimulated PBM cells. PBM DNA polymerase α was assayed in 100 ml reaction mixtures containing 100 μM Tris-HCl (pH 8.0), 6 mM MgCl$_2$, 5 mM dithiothreitol, 400 μg/ml BSA, 1 μM[$^3$H]dCTP (specific activity 25 Ci/mmol), 100 μM each of dATP, dTTP, and dGTP, and 200 μg of activated calf thymus DNA per ml. Reactions were started by the addition of 10 μl of enzyme. The reaction mixtures were incubated and process as described in *Antimicrob. Agents Chemother*, 33:115–117 (1989), using standard techniques.

The interaction of the 5'-triphosphate of AzddMeC and the HIV-1 reverse transcriptase in synthesis directed by (rl)$_n$.(dC)$_{12-18}$ as template indicated a competitive inhibition pattern with respect to dCTP, and an affinity about 30-fold greater than that for ddCTP. The values of the inhibition constant, K$_{is}$, as determined from the replot of slopes versus inhibitor concentration, were 0.0093 mM and 0.29 mM for AzddMeC-TP and ddCTP, respectively. The calculated mean Km for dCTP was about 7.2 μM (range 5.3–9.1 μM). Kinetic studies of AzddMeC and ddCTP on cellular DNA polymerase α activity revealed that both compounds were competitive inhibitors with respect to the varied concentrations of dCTP. However, significantly higher concentrations of the compounds were required for a 50% reduction of DNA polymerase α activity. AzddMeC-TP inhibited HIV-1 RT by 50% at a concentration 6,000-fold lower than that which was required for a similar inhibition of DNA polymerase α.

EXAMPLE 5

Intracellular metabolism of AzddMeC

AzddMeC is deaminated to AZT. Because AzddMeC is not toxic to human bone marrow cells in vitro, it must have a different metabolism from AZT, which is toxic to bone marrow in vivo. AzddMeC had been determined not to be a substrate for cytidine deaminase derived from HEp-2 cells.

The results are shown in Table II.

TABLE II

Metabolism of 10 μM [$^3$H]-AzddMeC in human cells after 24 hour exposure*.

| Compounds: | | | | |
|---|---|---|---|---|
| AzddMeC | AZT | AZT-MP | AZT-DDP | AZT-TP |
| Peripheral Blood Mononuclear Cells | | | | |
| 5.05 | 1.35 | | | |

TABLE II-continued

Metabolism of 10 μM [$^3$H]-AzddMeC in human cells after 24 hour exposure*.

| Compounds: | | | | |
|---|---|---|---|---|
| AzddMeC | AZT | AZT-MP | AZT-DDP | AZT-TP |
| (total of 11.4) | | 19.4 | 0.32 | 0.30 |
| Human Bone Marrow Cells | | | | |
| (1.88 total) | | 4.81 | N.D. | N.D. |
| 2.0 | 0.71 | | (8.16 total) | |

*pmoles/10$^6$ cells.
N.D. Not detected.

Metabolic studies in PBM cells show that the major metabolite of AzddMeC is AZT-monophosphate (AZT-MP), with no formation of AzddMeC-MP. While both AZT-diphosphate (AZT-DP) and AZT-triphosphate (AZT-TP) are formed in PBM cells, only AZT-MP is formed in bone marrow cells. In contrast, neither AZT-MP nor AzddMeC is detected in CEM cells.

This data suggests that AzddMeC is partially deaminated to AZT in the primary cells and that AZT-MP is generated by phosphorylation of AZT rather than deamination of AzddMeC-MP. While the main metabolite of AZT is AZT-MP, in primary cells treated with AzddMeC the ratio of AZT:AZT-MP is about 2:1. It therefore appears that AzddMeC may compete for phosphorylation with AZT.

EXAMPLE 6

In vivo toxicity in mice

BALB/c mice were treated ad libitum orally with either AZT or AzddMeC (0.1 mg/ml, equivalent to about 17.5 mg/kg per day). The continuous oral treatment with AzddMeC for 145 days produced no apparent toxicity. AZT produced an increase in mean corpuscular volume of red cells as early as 34 days after treatment (MCV±SD=51.7±0.3 fL versus 46.9±0.4 fL for water treated animals; n=5). A similar effect was not seen with AzddMeC (MCV=46.9±0.3 fL) even when the animals were evaluated 145 days after initiation of treatment. None of the animals lost weight or failed to gain weight after treatment with either AzddMeC or AZT, as compared to untreated mice.

EXAMPLE 7

Pharmacokinetics of AzddMeC in rats and rhesus monkeys

The preclinical pharmacokinetics of AzddMeC were characterized after intravenous administration to rats and after intravenous and oral drug administration to monkeys. AzddMeC was administered intravenously at doses of 10, 50 and 100 mg/kg. Plasma and urine concentrations of AzddMeC were determined by HPLC and pharmacokinetic parameters generated by area/-moment analysis.

Standard techniques were used with 250–350 g adult male Sprague-Dawley rats. Drug was administered via external jugular vein cannulas surgically implanted. AzddMeC was administered in 1.0 ml normal saline over 30 seconds. Six rats were studied at each does. 0.3 ml blood samples were collected prior to and at 0.08, 0.25, 0.5, 0.75, 1, 1.5, 2, 3, 4, 5, 6, 7, 8, 10 and 12 h following drug administration from the cannula into heparinized polypropylene microcentrifuge tubes. Blood volume was replaced with normal saline. Blood samples were centrifuged and plasma frozen until analysis. Urine was collected at selected times 24 h after drug administration. Urine volume was measured and samples frozen until analyzed.

Drug concentrations in plasma and urine were determined by high-performance liquid chromatography (HPLC). 100 microliters of plasma, 50 microliters of control and 100 microliters of 2M perchloric acid as a protein precipitant were added to polypropylene microcentrifuge tubes (400 µl), mixed thoroughly and centrifuged at 5,000 g for 5 min. The supernatant (15-200 µl) was injected onto the HPLC (Waters Associates, Milford, MA). Chromatography was performed on an Alltech Hypersil ODS Column (0.46×15 cm, micron particle size) with a mobile phase consisting of 12% acetonitrile in 40 mM sodium acetate, pH 7.0, at a flow rate of 2 ml/min. Compounds were quantitated at a UV wavelength of 283 nm with a detector range setting of 0.005 AUFS. Retention times for AzddMeC was 2.6 min. AZT had a retention time of 4.1 min.

Urine samples were diluted to 1:100 with deionized distilled water, internal standard was added and 20-100 µl of sample was injected into the HPLC. Drug concentration was multiplied by volume of urine collected to determine the amount of unchanged AzddMeC excreted.

The potential formation of AzddMeC glucuronide in urine was ascertained by hydrolysis with β-glucuronidase. Urine (100 µl), 15 µl 0.12N acetic acid, 100 µl β-glucuronidase (500 units per ml in water), and 35 µl phosphate buffer, pH 5.8 were added to glass culture tubes, mixed and incubated with gentle shaking at 37° C. in a water bath for 12 h. β-glucuronidase treated urine was assayed for AzddMeC as described for urine samples. Glucuronide concentration was calculated as the difference between nucleoside concentrations before and after hydrolysis with β-glucuronidase.

The AzddMeC standards ranging from 0.1 to 100 µl g/ml were prepared in blank rat plasma and urine. Standard curve slopes and intercepts were generated by weighted (1/Y) least squares limit linear regression. The assay was linear in the range of 0.1 to 100 µl g/ml, and the lower limit of quantitation was 0.1 µg/ml (10 ng). Plasma samples with AzddMeC concentrations exceeding 100 µl/ml were diluted with blank rat plasma before being assayed. Extraction and recovery of AzddMeC and internal standard was 85%. The intra- and inter-day coefficients of variation for the assay were less than 10% at all drug concentrations.

Area/moment analysis was used to calculate the pharmacokinetic parameters of AzddMeC. Area under the plasma concentration-time curve (AUG) and first non-normalized moment (AUMC) were determined by Lagrange polynomial interpolation integration from time zero to the last sample time with extrapolation to time infinity using the NONLIN least squares terminal slope. Total clearance ($CL_T$) was calculated from Dose/AUC, mean residence time (MRT) from AUMC/AUC and steady-state volume of distribution (Vss) from $CL_T \times MRT$. The fraction of drug excreted unchanged in urine (fe) was calculated from Au/Dose, where Au is the amount of AzddMeC excreted to time infinity. Renal clearance ($CL_R$) was calculated from $fe \times CL_T$, and non-renal clearance ($CL_{NR}$) from $CL_T - CL_R$. Half-life ($T_{\frac{1}{2}}$) was calculated from $0.693/\lambda z$, where $\lambda z$ is the NONLIN least-squares terminal slope.

Statistical analysis was performed using a one-way analysis of variance comparing the effects of dose. A probability level of less than 0.05 was considered statistically significant.

Figure 2:
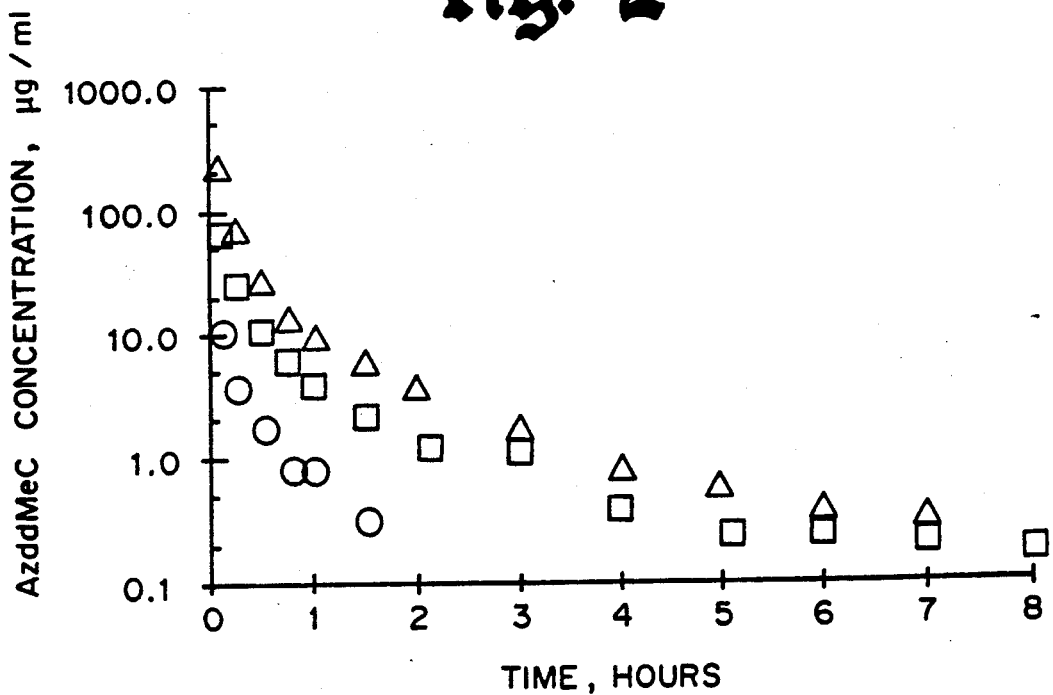
FIG. 2 is a graph comparing the plasma concentration in rats of AzddMeC in mg/ml over time (hours). (◯), 10 mg/kg; (□), 50 mg/kg; and (△), 100 mg/kg intravenous dose.
Figure 1A:
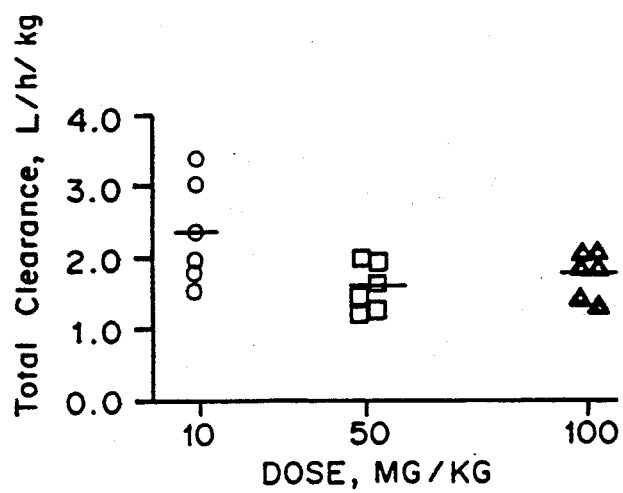
Figure 1B:
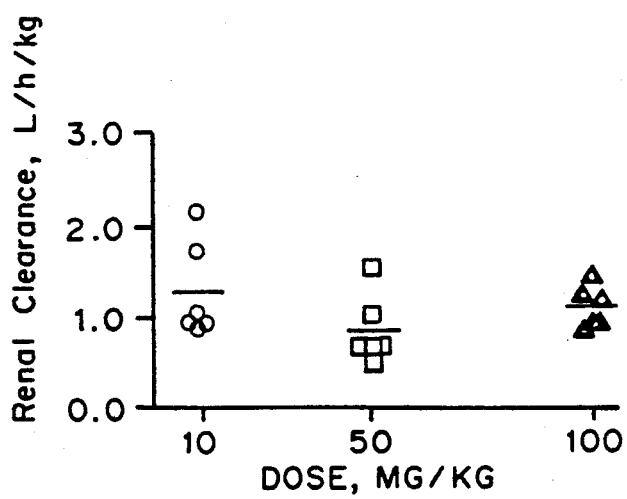
Figure 1C:
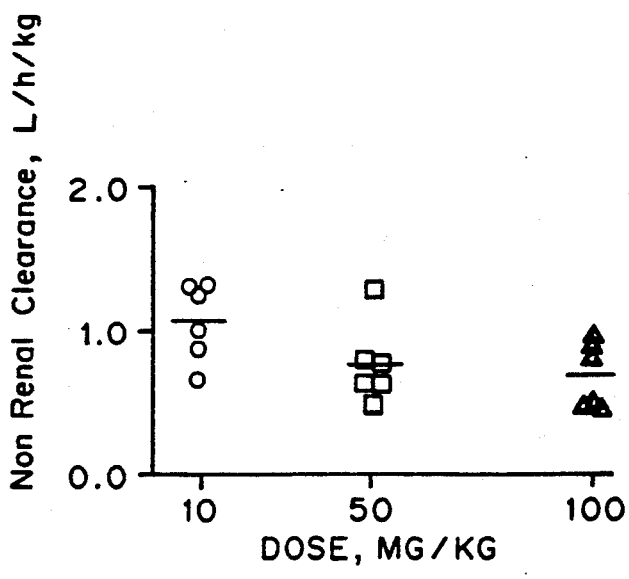

FIG. 2 demonstrates the plasma concentrations of AzddMeC over eight hours. Following intravenous administration of AzddMeC to rats, total clearance averaged 1.9±0.57 L/h/kg (mean±SD of 18 rats) and steady-state volume of distribution was 1.4±0.64 L/kg. Half-life averaged 2.5±1.5 h. No statistically significant differences were noted in pharmacokinetic parameters between the three doses. Total clearance was 2.33±0.73 (mean±SD), 1.57±0.33, and 1.76±0.32 L/h/kg after 10, 50, and 100 mg AzddMeC/kg body weight, respectively, as shown in FIG. 3A. Renal excretion accounted for approximately half of the total clearance with 55±11% of the dose recovered as unchanged AzddMeC in the urine, as shown in FIG. 3B. Non-renal clearance is shown in FIG. 3C. No glucuronide metabolite was found in urine. In addition, AzddMeC was not metabolized by deamination to AZT in rats. Steady-state volume of distribution of AzddMeC average 0.92±0.27, 1.73±0.78, and 1.46±0.44 L/kg following administration of 10, 50, and 100 mg AzddMeC/kg body weight, respectively. These results indicated that the disposition of AzddMeC in rats is independent of dose over the range of 10–100 mg/kg. The pharmacokinetics of AzddMeC in rats are similar to those of 2', 3'-dideoxycytidine while the clearance of AzddMeC is 40% less than that of AZT.

The disposition of AzddMeC was then assessed after intravenous and oral administration of 60 mg/kg AzddMeC to rhesus monkeys, as described with respect to the rats. Bioavailability (F) after oral and subcutaneous drug administration was calculated from $AUC_{PO,SSQ} \times Dose_{iv}/AUC_{iv} \times Dose_{PO,SQ}$. For bioavailability, $CI_T$ was assumed to be independent of dose.

The mean half-life for AzddMeC was 1.52±0.73 (mean±SD for three monkeys) and 1.74±1.0 h after intravenous and oral administration, respectively. Total clearance after intravenous AzddMeC was 2.2±0.12 L/h/kg and steady-state volume of distribution was 1.2±0.53 L/kg. The oral bioavailability was 21±8%. AZT appeared to be a major metabolite of AzddMeC, suggesting that the nucleoside is deaminated to a significant degree in monkeys. No glucuronide metabolite of AzddMeC was detected in the urine, however, a significant amount of AZT glucuronide was found in the urine. Although AzddMeC was not found in the cerebral spinal fluid (CSF), AZT could be detected. These results are summarized in Table III.

TABLE III

Pharmacokinetic parameters in rhesus monkeys after intravenous and oral administration of 60 mg AzddMeC/kg body weight, compared with AZT.

| Parameter | RHD-1 Monkey | | RIJJ-1 | | RZO-1 | |
|---|---|---|---|---|---|---|
| Route: | IV | PO | IV | PO | IV | PO |
| AzddMeC: | | | | | | |
| Dose, mg/kg | 60 | 60 | 60 | 60 | 60 | 60 |
| AUC, mg.h/L | 27.6 | 3.39 | 28.7 | 7.69 | 25.9 | 6.39 |
| $Cl_T$, L/h/kg | 2.17 | | 2.09 | | 2.32 | |
| $V_{ss}$, L/kg | 0.62 | | 1.65 | | 1.33 | |
| $t_{\frac{1}{2}}$, h | 0.68 | 0.68 | 1.98 | 2.66 | 1.89 | 1.87 |
| F | | 0.12 | | 0.27 | | 0.25 |
| AZT: | | | | | | |
| AUC, mg.h/L | 13.4 | 1.39 | 13.5 | 2.09 | 9.99 | 1.61 |
| $t_{\frac{1}{2}}$, h | 0.61 | 0.61 | 0.74 | 1.57 | 0.52 | 0.91 |
| AUC (AZT) | 0.49 | 0.41 | 0.47 | 0.27 | 0.39 | 0.25 |

TABLE III-continued

Pharmacokinetic parameters in rhesus monkeys after intravenous and oral administration of 60 mg AzddMeC/kg body weight, compared with AZT.

| | Monkey | | | | | |
|---|---|---|---|---|---|---|
| Parameter | RHD-1 | | RIJJ-1 | | RZO-1 | |
| Route: | IV | PO | IV | PO | IV | PO |
| AUC (AzddMeC) | | | | | | |

EXAMPLE 8

Uptake of AZT and AzddMeC in human PBM and conversion of AzddMeC to AZT

Figure 4:
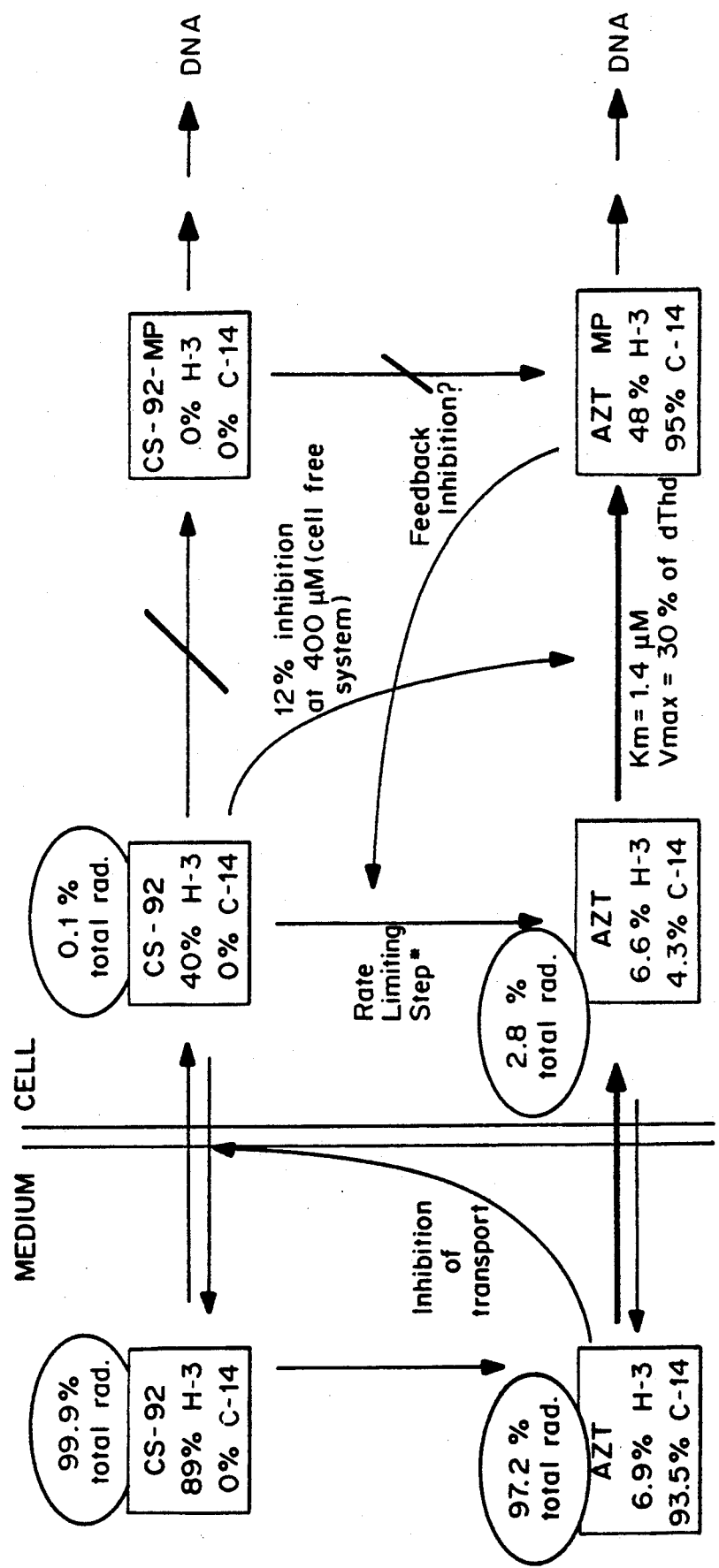
FIG. 4 diagrams the intracellular conversion of AzddMeC into AZT and then into AZT-MP, comparing uptake of radiolabelled AZT and AzdMeC by human blood mononuclear cells, 4 $\mu$M, for six hours.

The uptake of AZT, labelled with 14C,( and AzddMeC, labelled with $^3H$), by human peripheral blood mononuclear cells, over at period of 6 h at 4 μM, is compared in FIG. 4.

Figure 5A:
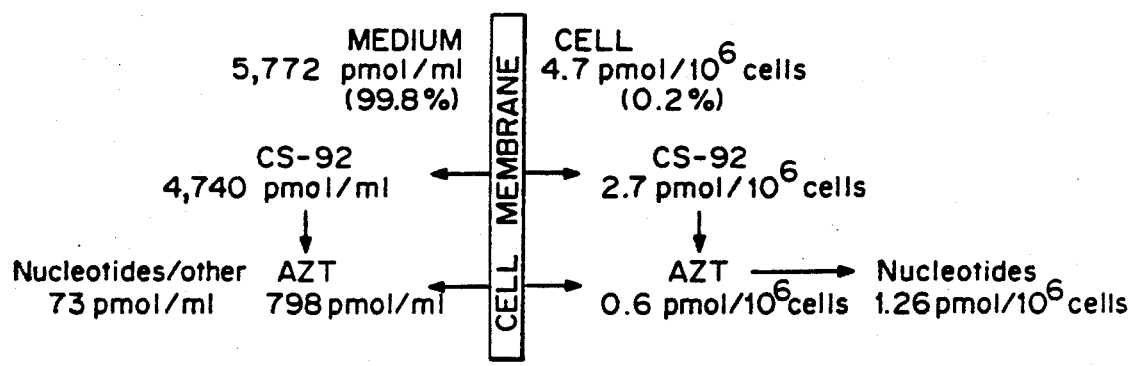
FIG. 5 A and 5 B demonstrate the preferential uptake of the AzddMeC (FIG. 5A) by PBM cells, as compared with AZT (FIG. 5B), six hour incubation at 37° C. with 10 $\mu$M.
Figure 5B:
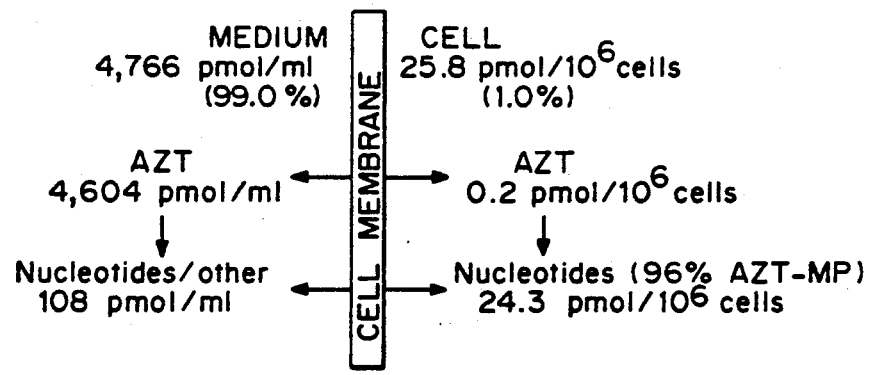
Figure 6:
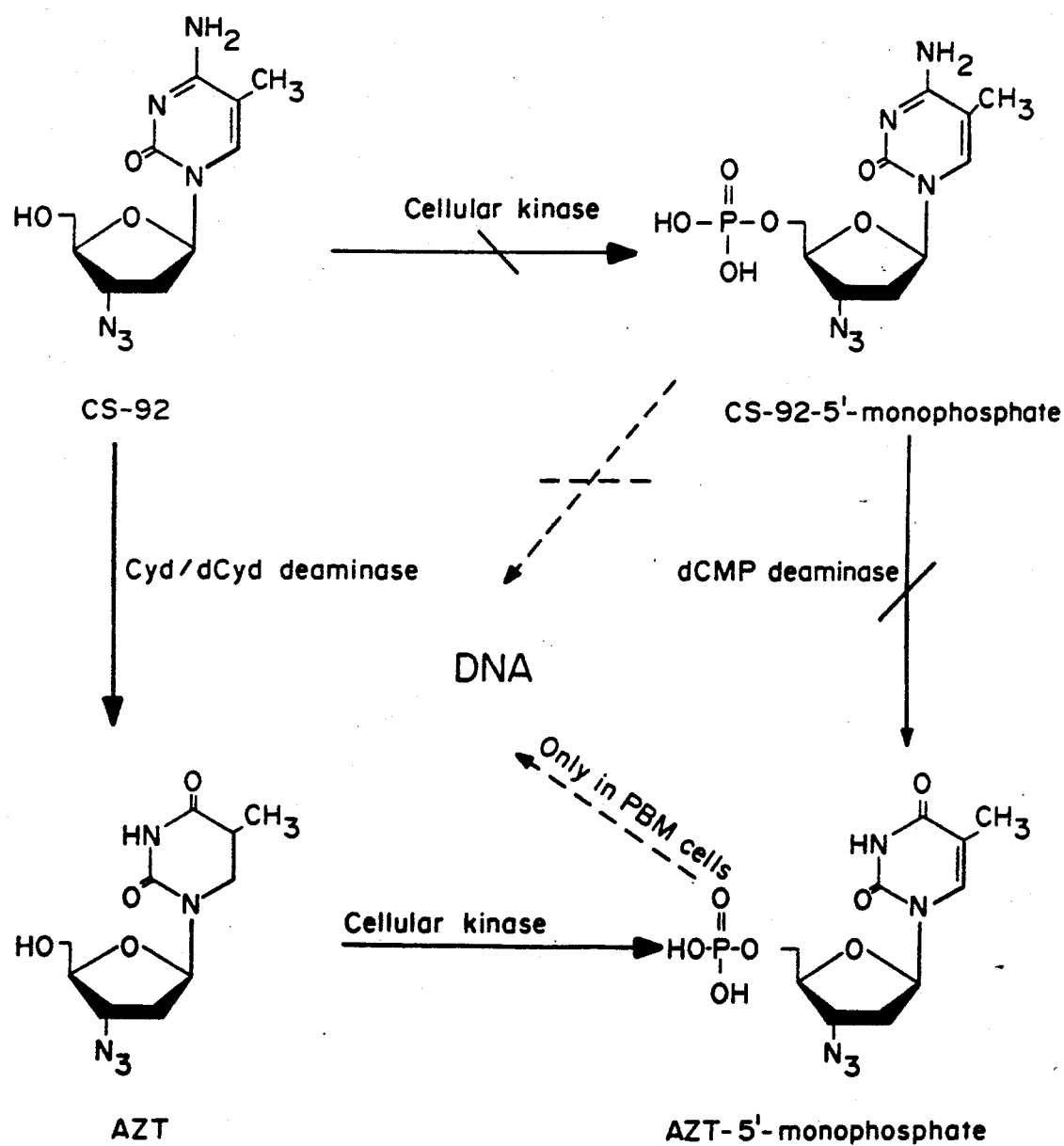
FIG. 6 diagrams the proposed mechanism for the bioconversion of AzddMeC in PBM and bone marrow cells in vitro.

The results shown in FIG. 4 demonstrate that AzddMeC is converted intracellularly into AZT (6.6%) and then into AZT-MP (48%). In a cell free assay, 0.35% of the AzddMeC is deaminated to AZT. The conversion of AzddMeC into the AZT is the rate limiting step. At 400 μM, there is 12% inhibition of the phosphorylation of AZT into AZT-MP in a cell free system. Very little of the AZT in the medium (6.9%) is converted from AzddMeC. FIG. 5 demonstrates the preferential uptake of the AzddMeC by PBM cells, as compared with AZT. FIG. 6 diagrams the proposed mechanism for the bioconversion of AzddMeC in PBM and bone marrow cells.

EXAMPLE 9

Preparation of a Pharmaceutical Composition containing AzddMeC as the active agent for treatment of HIV infection HIV infection can be treated by administering to the patient an effective amount of 3'-azido-2',3'-dideoxy-5-methylcytidine or its salts in the presence of a pharmaceutically acceptable carrier or diluent.

The active materials can be administered by any appropriate route, for example, orally, parenterally, intravenously, intradermally, subcutaneously, or topically, in liquid or solid form. The composition is preferably administered orally.

The active compound is included in the pharmaceutically acceptable carrier or in an amount to inhibit HIV replication in vivo in the absence of serious toxic effects. By "HIV inhibitory amount" is meant an amount of active ingredient sufficient to exert an HIV inhibitory effect as measured by, for example, an assay such as the ones described herein.

These preparations should produce a serum concentration of active ingredient of from about 0.2 to 40 μM. A preferred concentration range is from 0.2 to 20 μM and most preferably about 1 to 10 μM. The pharmaceutical compositions should provide a dosage of from 1 to 60 milligrams of compound per kilogram of body weight per day.

As demonstrated by the examples above, the amount of AzddMeC that will be administered per day is significantly less than predicted based on the cell culture data, since the half-life is two to three times as great as AZT. However, there should be no question of efficacy since the compound is converted intracellularly into AZT, which has been approved by the Food and Drug Administration for treatment of AIDS. Moreover, administration of AzddMeC is a method of preferentially delivering AZT intracellularly to PBM and other blood cells besides the bone marrow precursor cells and erythroid precursor cells.

Dosage values will depend somewhat on the patient and the severity of the condition to be alleviated. It is understood that for any particular subject, specific dosage regimens should be adjusted over time according to the individual need and the professional judgment of the person administering the active composition.

3'-Azido-2',3'-dideoxy-5-methylcytidine can also be mixed with other active materials which do not impair the desired action, or with materials that supplement the desired action, such as antibiotics, antifungals, antiinflammatories, or other antivirals, including other nucleoside anti-HIV compounds. It is believed that a mixture of AZT and AzddMeC may be particularly preferred since AzddMeC does not penetrate the CNS and AZT does.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder, an excipient, a disintegrating agent, a lubricant, a glidant, a sweetening agent, or a flavoring agent.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents. Pharmaceutically acceptable vehicles for intravenous or subcutaneous administration are also known. If administered intravenously, preferred carriers are physiological saline or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811. For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of 3'-azido-2',3'-dideoxy-5-methylcytidine or its monophosphate, diphosphate, and/or triphosphate derivatives are then introduced into the container. The container is then swirled by hand to free lipid material from the sides of the container and to disperse lipid aggregates, thereby forming the liposomal suspension.

EXAMPLE 9

Preparation of Phosphate Derivatives of AzddMeC

The phosphate derivatives of AzddMeC are prepared by phosphorylation of 3'-azido-2,3-dideoxy-5-methylcytidine as described below.

The monophosphate can be prepared according to the procedure of Imai et al., *J. Org. Chem.*, 34(6), 1547–1550 (June 1969). For example, about 100 mg of AzddMeC and about 280 I of phosphoryl chloride are reacted with stirring in about 8 ml of dry ethyl acetate at about 0° C. for about four hours. The reaction is quenched with ice. The aqueous phase is purified on an activated charcoal column, eluting with 5% ammonium hydroxide in a 1:1 mixture of ethanol and water. Evaporation of the eluant gives 100 mg of the ammonium-(3'-azido-2',3'-dideoxy-5-methylcytidine)-5'-monophosphate.

The diphosphate can be prepared according to the procedure of Davisson et al., *J. Org. Chem.*, 52(9), 1794–1801 (1987). 3'-azido-2',3'-dideoxy-5-methylcytidine-5'-diphosphate may be prepared from the tosylate of AzddMeC, which may be prepared, for example, by reacting AzddMeC with tosyl chloride in pyridine at room temperature for about 24 hours, working up the product in the usual manner (e.g., by washing, drying, and crystallizing it).

The triphosphate can be prepared according to the procedure of Hoard et al., *J. Am. Chem. Soc.*, 87(8), 1785–1788 (1965). For example, 3'-azido-2',3'-dideoxymethylcytidine-5'-monophosphate is activated (by making a imidazolide, according to methods known to those skilled in the art) and treating with tributyl ammonium pyrophosphate in DMF. The reaction gives primarily 3'-azido-2',3'-dideoxy-5-methylcytidine -5'-triphosphate, with some unreacted monophosphate and some diphosphate. Purification by anion exchange chromatography of a DEAE column is followed by isolation of AzddMeC as the triphosphate, e.g., as the tetrasodium salt.

Structurally related analogues such as phosphorylated and acylated derivatives of AzddMeC, and C-nucleoside derivatives thereof will have similar activities at generally the same in vivo concentration ranges.

Modifications and variations of the present invention relating to compositions for the treatment of HIV which include 3'-azido-2',3'-dideoxy-5-methylcytidine as the active antiviral agent, and the method of use thereof, will be obvious to those skilled in the art from the foregoing detailed description of the invention, and are intended to come within the scope of the appended claims.

We claim:

1. A composition comprising a pharmaceutically acceptable carrier for delivering to humans an effective amount to inhibit human immunodeficiency virus replication of a compound of the formula:

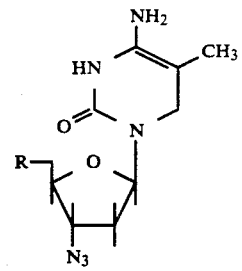

wherein R is OH, monophosphate, diphosphate, or triphosphate or a pharmacologically acceptable salt thereof.

2. The composition of claim 1, wherein the carrier further comprises a material selected from the group consisting of a binder, an excipient, a disintegrating agent, a lubricant, a glidant and an adjuvant.

3. The composition of claim 1, wherein the carrier is selected from the group consisting of oil, water, saline, phosphate buffer, polyethylene glycol, glycerine, propylene glycol, and combinations thereof.

4. The composition of claim 1, wherein the carrier comprises a controlled release formulation which protects the compound against rapid elimination from the body.

5. The composition of claim 1 which, after administration to a human, produces a blood serum concentration of compound of between approximately 0.2 and 40 $\mu M$.

6. The composition of claim 1 which, after administration to a human, produces a blood serum concentration of compound between approximately 0.2 and 20 $\mu M$.

7. The composition of claim 1 further comprising 3'-azido-3'-deoxythymidine (AZT).

8. A method for inhibiting replication of HIV in cells comprising the step of administering to humans an effective amount to inhibit human immunodeficiency virus replication of a compound having the formula:

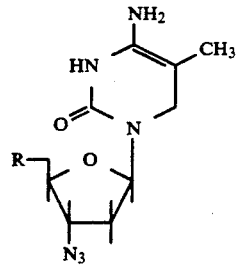

wherein R is OH, monophosphate, diphosphate, or triphosphate or a pharmacologically acceptable salt thereof, in combination with 3'-azido-3'-deoxythymidine (AZT).

* * * * *